(12) United States Patent
Altevogt et al.

(10) Patent No.: US 8,568,994 B2
(45) Date of Patent: Oct. 29, 2013

(54) METHOD FOR PRENATAL DIAGNOSIS

(75) Inventors: Peter Altevogt, Neckargemünd (DE); Sascha Keller, St. Leon (DE)

(73) Assignee: DKFZ Deutsches Krebsforschungszentrum, Stiftung des Offentlichen Rechts, Heidelberg (DE)

( * ) Notice: Subject to any disclaimer, the term of this patent is extended or adjusted under 35 U.S.C. 154(b) by 582 days.

(21) Appl. No.: 12/671,196

(22) PCT Filed: Aug. 1, 2008

(86) PCT No.: PCT/EP2008/060145
§ 371 (c)(1),
(2), (4) Date: Jul. 14, 2010

(87) PCT Pub. No.: WO2009/019215
PCT Pub. Date: Feb. 12, 2009

(65) Prior Publication Data
US 2010/0279315 A1    Nov. 4, 2010

(30) Foreign Application Priority Data
Aug. 3, 2007 (EP) .................................. 07015323

(51) Int. Cl.
*G01N 33/567* (2006.01)
*G01N 33/48* (2006.01)
*G01N 1/18* (2006.01)

(52) U.S. Cl.
USPC ............ 435/7.21; 435/6; 435/7.23; 435/7.24; 435/7.25; 435/372.2; 435/372.3; 436/63; 436/64; 436/177; 436/811; 436/813; 436/814

(58) Field of Classification Search
USPC .......... 435/6, 7.2, 7.23, 7.24, 372.2, 372.3, 1, 435/7.25; 436/547, 548, 63, 64, 177, 811, 436/813, 814
See application file for complete search history.

(56) References Cited

U.S. PATENT DOCUMENTS

2007/0161125 A1    7/2007    Rosenfeld et al.

OTHER PUBLICATIONS

EXBIO Product Technical Information (2003).*
Bodey et al. Dendritic type, accessory cells within the mammalian thymic microenvironment. Antigen presentation in the dendritic neuro-endocrine-immune cellular network, In Vivo 11 (4): 351-370 (Jul.-Aug. 1997) (Abstract Only).*
Thery et al. Isolation and Characterization of Exosomes from Cell Culture Supernatants and Biological Fluids, Cell Biology, Supplement 30, p. 3.22.1-3.22.29 (2006).*
Koga et al. Purification, Characterization and Biological Significance of Tumor-derived Exosomes. AntiCancer Research 25: 3703-3708 (2005).*
Thery et al., "Exosomes: composition, biogenesis and function," *Nat. Rev. Immunol.*, vol. 2, pp. 569-579 (2002).
Andre et al., "Malignant effusions and immunogenic tumour-derived exosomes," *Lancet*, vol. 360, pp. 295-305 (2002).
Raiborg et al., "Protein sorting into multivesicular endosomes," *Curr. Opin. Cell. Bio.*, vol. 15, pp. 446-455 (2003).

(Continued)

Primary Examiner — Gail R Gabel
(74) Attorney, Agent, or Firm — Foley & Lardner LLP

(57) ABSTRACT

The invention discloses a method of prenatal diagnosis comprising the step of isolating exosomes from an isolated fluid, wherein the exosomes are identified by biomarker detection. Furthermore, the invention discloses the isolation of exosomes from an isolated fluid and the use of a biomarker, particularly CD24 to isolate exosomes from an isolated fluid.

10 Claims, 15 Drawing Sheets

(56) References Cited

OTHER PUBLICATIONS

Figure 1:
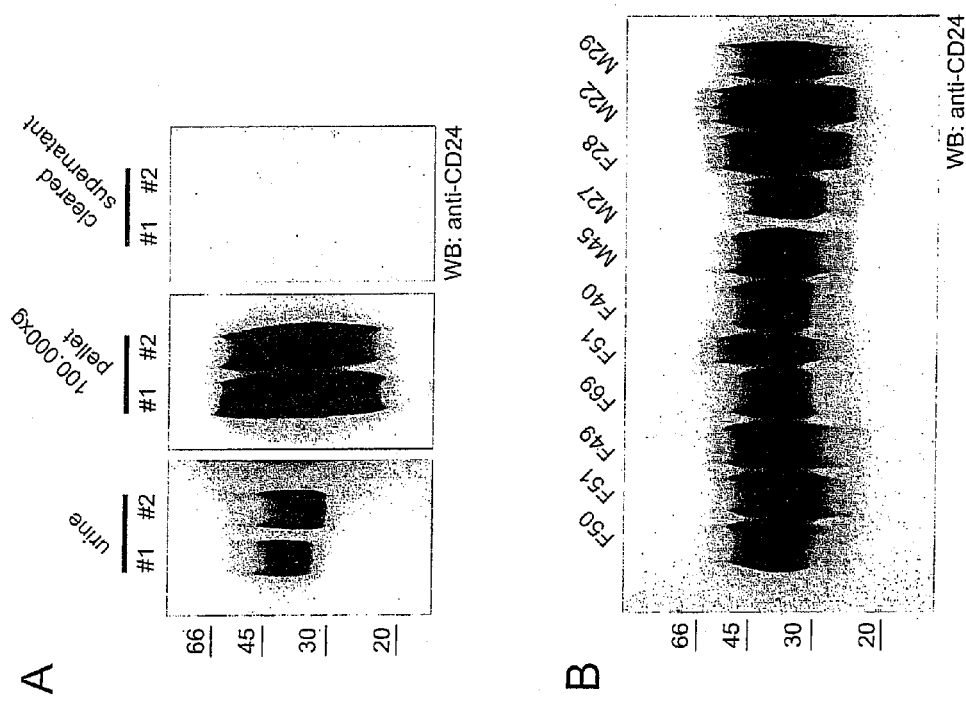
Figure 1:
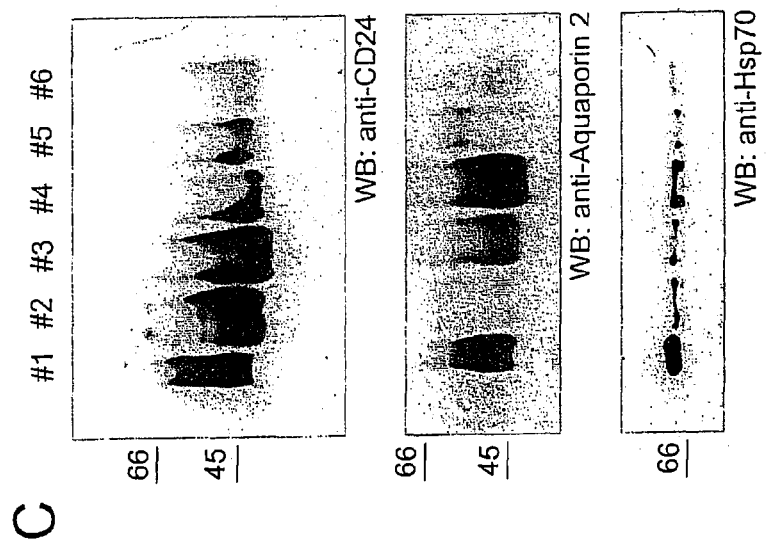

Ginestra et al., "The amount and proteolytic content of vesicles shed by human cancer cell lines correlates with their in vitro invasiveness," Anticancer Res., vol. 18, pp. 3433-3437 (1998).
Keller et al., "Exosomes: From biogenesis and secretion to biological function," Immunol. Lett., vol. 107, pp. 102-108 (2006).
Caby et al., "Exosomal-like vesicles are present in human blood plasma," Int. Immunol., vol. 17, pp. 879-887 (2005).
Gutwein, et al., "Cleavage of L1 in exosomes and apoptotic membrane vesicles released from ovarian carcinoma cells," Clin. Cancer Res., vol. 11, pp. 2492-2501 (2005).
Pisitkun et al., "Identification and proteomic profiling of exosomes in human urine," Proc. Nat. Acad. Sci., USA, vol. 101, pp. 13368-13373 (2004).
Stoorvogel et al., "The biogenesis and functions of exosomes," Traffic, vol. 3, pp. 321-330 (2002).
de Gassart et al., Exosome secretion: the art of reutilizing nonrecycled proteins?, Traffic, vol. 5, pp. 896-890 (2004).
Dolo et al., "Selective localization of matrix metalloproteinase 9, $\beta_1$ integrins, and human lymphocyte antigen class I molecules on membrane vesicles shed by 8701-BC breast carcinoma cells," Cancer Res., vol. 58, pp. 4468-4474 (1998).
Kristiansen et al., "Tumour biological aspects of CD24, a mucinlike adhesion molecule," J. Mol. Histo., vol. 35, pp. 255-262 (2004).
Schabath et al., "CD24 affects CXCR4 function in pre-B lymphocytes and breast carcinoma cells," J. Cell Sci., vol. 119, pp. 314-325 (2006).
de Gassart et al., "Lipid raft-associated protein sorting in exosomes," Blood, vol. 102, pp. 4336-4344 (2003).
Gutwein et al., "ADAMIO-mediated cleavage of L1 adhesion molecule at the cell surface and in released membrane vesicles," Faseb. J., vol. 17, pp. 292-294 (2003).
Stoeck et al., "A role for exosomes in the constitutive and stimulus-induced ectodomain cleavage of L1 and CD44," Biochem J., vol. 393, pp. 609-618 (2006).
Hoorn et al., "Prospects for urinary proteomics: exosomes as a source of urinary biomarkers," Nephrology, vol. 10, pp. 283-290 (2005).
Adachi et al., "The human urinary proteome contains more than 1500 proteins, including a large proportion of membrane proteins," Genome Bio., vol. 7, pp. R80.1-R80.16 (2006).
Safaei et al., "Abnormal lysosomal trafficking and enhanced exosomal export of cisplatin in drug-resistant human ovarian carcinoma cells," Mol Cancer Ther., vol. 4, pp. 1595-1604 (2005).
Shedden et al., "Expulsion of small molecules in vesicles shed by cancer cells: association with gene expression and chemosensitivity profiles," Cancer Res., vol. 63, pp. 4331-4337 (2003).
Li et al., "Role of exosomes in immune regulation," J. Cell Mol. Med., vol. 10, pp. 364-375 (2006).
Taylor et al., "Pregnancy-associated exosomes and their modulation of T cell signaling," J. Immunol., vol. 176, pp. 1534-1542 (2006).
Zitvogel et al., "Dendritic cell-based immunotherapy of cancer," Ann. Oncol., vol. 11, pp. 199-205 (2000).
Kovar et al., "Direct stimulation of T cells by membrane vesicles from antigen-presenting cells," Proc. Nat. Acad. Sci., USA, vol. 103, pp. 11671-11676 (2006).
Andreola et al., "Induction of lymphocyte apoptosis by tumor cell secretion of FasL-bearing microvesicles," J. Exp. Med., vol. 195, pp. 1303-1316 (2002).
Liu et al., "Murine mammary carcinoma exosomes promote tumor growth by suppression of NK cell function," J. Immunol., vol. 176, pp. 1375-1385 (2006).
Hanna et al., "Decidual NK cells regulate key developmental processes at the human fetal-maternal interface," Nat. Med., vol. 12, pp. 1065-1074, including Supplemental Fig. 1-2, Supplemental Table 2-4, Supplemental Methods (2006).
Valadi et al., "Exosome-mediated transfer of MRNAs and microRNAs is a novel mechanism of genetic exchange between cells," Nature Cell Bio, vol. 7, pp. 654-659, Supplemental Information, 11 pgs. (2007).
Kadmon et al., "Nectadrin, the heat-stable antigen, is a cell adhesion molecule," J. Cell Bio., vol. 118, pp. 1245-1258 (1992).
Saleem et al., "A conditionally immortalized human prodocyte cell line demonstrating nephrin and podocin expression," J. Am. Soc. Nephrol., vol. 13, pp. 630-638 (2002).
Blanchard et al., "TCR activation of human T cells induces the production of exosomes bearing the TCR/CD3/zeta complex," J. Immunol., vol. 168, pp. 3235-3241 (2002).
Fogel et al., "L1 expression as a predictor of progression and survival in patients with uterine and ovarian carcinomas," Lancet, vol. 362, pp. 869-875 (2003).
Keller et al., "CD24 is a marker of exosomes secreted into urine and amniotic fluid," Kidney International, vol. 72, No. 9, pp. 1095-1102 (2007).
Runz et al., "Malignant ascites-derived exosomes of ovarian carcinoma patients contain CD24 and EpCAM," Gyneologic Oncology, vol. 107, pp. 563-571 (2007).
Redman et al., "Circulating Microparticles in Normal Pregnancy and Pre-Eclampsia" Placenta, vol. 29, pp. 73-77 (2008).
Humphries et al., "CD24," 3 pages, Oct. 14, 1999, http://mpr.nci.nih.gov/PROW/guide/270610370g.htm.

\* cited by examiner

SEQUENCE LISTING

<160> NUMBER OF SEQ ID NOS: 1

<210> SEQ ID NO 1
<211> LENGTH: 80
<212> TYPE: PRT
<213> ORGANISM: Homo sapiens

<400> SEQUENCE: 1

-continued

```
Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
            20                  25                  30

Thr Ser Ser Asn Ser Ser Gln Ser Thr Ser Asn Ser Gly Leu Ala Pro
        35                  40                  45

Asn Pro Thr Asn Ala Thr Thr Lys Ala Ala Gly Gly Ala Leu Gln Ser
    50                  55                  60

Thr Ala Ser Leu Phe Val Val Ser Leu Ser Leu Leu His Leu Tyr Ser
65                  70                  75                  80
```

METHOD FOR PRENATAL DIAGNOSIS

CROSS-REFERENCE TO RELATED APPLICATIONS

This application is the National Phase of International Patent Application No. PCT/EP2008/060145, filed on Aug. 1, 2008, which claims the benefit of priority from European Patent Application No. 07015323.4, filed on Aug. 3, 2007. The contents of these applications are incorporated herein by reference in their entirety.

The present invention refers to a novel method of diagnosing amniotic fluid and urine by analyzing CD24 positive exosomes.

Prenatal diagnosis employs a variety of techniques to determine the health and condition of an unborn fetus. One major application concerns the prenatal detection of congenital diseases and anomalies. Without knowledge gained by prenatal diagnosis, there could be an untoward outcome for the fetus or the mother or both. Congenital anomalies account for 20 to 25% of perinatal deaths. The primary aim of prenatal diagnostic methods is focused on obtaining genetic information from the fetus or embryo. The methods used in clinical practice essentially involve invasive techniques such as ultrasonography, amniocentesis, chorionic villus sampling (CVS), maternal serum assays, and the removal of fetal blood or tissue biopsies. Those techniques involve obtaining samples directly from the fetus or indirectly from ovular structures. Because of the highly invasive nature of those methods, they are prone to complications for the mother or the fetus. Examples of such complications are the risk of infection, loss of amniotic fluid and abdominal pain. In order to limit the use of invasive prenatal diagnostic techniques risking the complications mentioned above, the development of novel methods constitutes a major aim in modern obstetrics.

The U.S. patent application US2007161125 provides non-invasive methods for the early diagnosis, prognosis, and monitoring of pathologic fetal or maternal conditions, by proteomic analysis of biological fluids and further provides proteomic profiles of biological fluids, such as amniotic fluid and maternal serum, which enable the diagnosis, prognosis, and monitoring of various pathologic fetal or maternal conditions. However, the application only discloses whole-amniotic fluid analysis, meaning that potential fetal determinants might be diluted out bearing the consequence that the results are not reliable and the amniocentesis might be repeated.

The object of the present invention is to provide a method which allows for a more accurate and reliable prenatal diagnosis by clearly assigning the genetic information obtained during analysis approach to the embryo and not to the mother.

The inventors of the present invention have now surprisingly found that amniotic fluid obtained from amniocentesis and urine from newborn contain small membrane vesicles, called exosomes, which have been clearly demonstrated to be derived from the fetus. Furthermore, they have found out that the genetic information of the fetus in the form of nucleic acids appears to be exclusively carried by these exosomes. As a general rule, cells appear to emit signals and communicate with each other via membrane vesicles that they release, which may carry genetic information from its origin, antigenic proteins (or polypeptides or peptides). These vesicles, particularly exosomes, thus represent a product of particular interest for diagnostic, vaccination or therapeutic applications or to deliver molecules of interest. Therefore, it would be of particular interest to have an effective method that could be used to enrich such vesicles compatible with biological use, particularly diagnostic and pharmacological use.

Using CD24 as marker, the inventors of the present invention detected exosomes in the urine of newborns and in amniotic fluids of pregnant women. These exosomes were derived from the kidney of the infant. Similar findings were made in the urine and amniotic fluid of mice. Genetic experiments using CD24 knockout mice further showed that CD24 positive exosomes were derived from the fetus and not from the mother. The amount of exosomes released into urine was similar in knockout mice or wild-type animals suggesting that CD24 was not essential for secretion. Their presence in embryonic development suggests that exosomes derived from the kidney of the embryo could play a biological role at the fetal-maternal interphase.

Accordingly, the problem is solved by the present invention, which provides a method for prenatal diagnosis comprising the step of isolating exosomes from an isolated fluid, wherein the exosomes are identified by biomarker detection.

"Prenatal diagnosis" refers to a variety of diagnostic methods that are performed during pregnancy in order to determine the health and condition of an unborn fetus as explained in more detail supra.

Within the context of this invention, the term "exosome" refers to externally released vesicles originating from the endosomic compartment or cells, including kidney cells, tumor cells and immune cells, particularly antigen presenting cells, such as dendritic cells, macrophages, mast cells, T lymphocytes or B lymphocytes. Exosomes are membrane vesicles with a size of 40-100 nm that are released from a variety of different cell types including tumor cells, red blood cells, platelets, lymphocytes, and dendritric cells (1,2). Exosomes are formed by invagination and budding from the limiting membrane of late endosomes (3). They accumulate in cytosolic multivesicular bodies (MVBs) from where they are released by fusion with the plasma membrane (3). The process of vesicle shedding is particularly active in proliferating cells, such as cancer cells, where the release can occur continuously (4). Depending on the cellular origin, exosomes recruit various cellular proteins that can be different from the plasma membrane including MHC molecules, tetraspanins, adhesion molecules and metalloproteinases (1,2,5). Exosomes have been found in various body fluids such as blood plasma (6), malignant ascites (7) and urine (8). It has been proposed that under physiological conditions exosomes could play a role in cell-cell interactions (9,10). When released from tumor cells, exosomes can promote invasion and migration (4,11).

More specifically, such vesicles are of endosomal origin and are secreted in the extracellular milieu following fusion of late endosomal multivesicular bodies with the plasma membrane. Methods of producing, purifying or using exosomes for therapeutic purposes or as research tools have been described in WO99/03499, WO00/44389 and WO97/05900, incorporated therein by reference.

As used herein, the term "fluid" includes, whole blood, sweat, tears, ear flow, sputum, lymph, bone marrow suspension, lymph, urine, saliva, semen, vaginal flow, cerebrospinal fluid, brain fluid, ascites, milk, secretions of the respiratory, intestinal and genitourinary tracts, and amniotic fluid. Preferably, a fluid sample derived from an animal is urine or amniotic fluid. When analyzing a fluid from an animal, the animal can be, for example, a domesticated animal, such as a cow, a chicken, a pig, a horse, a rabbit, a dog, a cat, and a goat. In preferred embodiments, the animal is a human.

Exosomes can be isolated from the surrounding fluid by methods well known in the art. Usually, exosomes are separated from the fluid by centrifugation. The skilled artisan is aware of the fact, that an efficient separation might require several centrifugation steps using different centrifugation procedures, temperatures, speeds, durations, rotors, and the like. Furthermore, the isolation might require further density gradient centrifugations. Density centrifugation uses a dense solution or density gradient to separate particles based on their individual densities or mass/size ratio. A solution is prepared such that a gradient of densities is available for particles to pass through or float upon. This density gradient may be continuous or prepared in a stepped manner such as the layers in a parfait. The homogenate, prepared in a dilute buffer and centrifuged briefly to remove tissue and unbroken cells, is then layered on top. After centrifugation typically for an hour at about 100,000×g, one can observe disks of cellular components residing at the change in density from one layer to the next. By carefully adjusting the layer densities to match the cell type, one can enrich nuclear, mitochondrial, microsomal, and plasma membrane vesicle fractions. In a preferred embodiment of the present invention, different layers of sucrose are used as separating cushion as described in the examples (Materials and methods). It is to be understood that the concentrations of sucrose might be adjusted from experiment to experiment.

Generally, the term "biomarker" refers to any genetically controlled difference which can be used in the genetic analysis of a test versus a control sample, for the purpose of assigning the sample to a defined genotype or phenotype. As used herein, "biomarkers" refer to genes which are expressed within or at the lipid bilayer of exosomes. The biomarkers can be defined by their gene symbol name, their encoded protein name, their transcript identification number (cluster identification number), the data base accession number, public accession number or GenBank (NCBI, National Center for Biotechnology Information, http://www.ncbi.nlm.nih.gov) identifier or chromosomal location, UniGene accession number and cluster type, LocusLink accession number.

Generally, the expression level of a biomarker is determined by the determining the expression of its corresponding "polynucleotide" or "polypeptide" as described hereinafter.

For the purposes of the present invention, the biomarker is preferably determined by determining the expression of its corresponding polypeptide. The expression of the biomarker is detected using a compound which specifically binds to it. As used herein, "specifically binding" means that the compound is capable of discriminating between two or more polypeptides, i.e. it binds to the desired polypeptide, but essentially does not bind unspecifically to a different polypeptide. The compound can be an antibody, or a fragment thereof, an enzyme, a so-called small molecule compound, a protein-scaffold, preferably an anticalin. In a preferred embodiment, the compound specifically binding to the polypeptide is an antibody, or a fragment thereof.

As used herein, an "antibody" comprises monoclonal antibodies as first described by Köhler and Milstein in Nature 278 (1975), 495-497 as well as polyclonal antibodies, i.e. antibodies contained in a polyclonal antiserum. Monoclonal antibodies include those produced by transgenic mice. Fragments of antibodies include F(ab')$_2$, Fab and Fv fragments. Derivatives of antibodies include scFvs, chimeric and humanized antibodies.

See, for example Harlow and Lane, loc. cit. For the detection of polypeptides using antibodies or fragments thereof, the person skilled in the art is aware of a variety of methods, all of which are included in the present invention. Examples include immunohistochemistry, immunoprecipitation, Western blotting, Enzyme-linked immuno sorbent assay (ELISA), radio immuno assay (RIA), dissociation-enhanced lanthanide fluoro immuno assay (DELFIA), scintillation proximity assay (SPA). For detection, it is desirable if the antibody is labelled.

In a preferred embodiment, the biomarker is a GPI-anchored protein. Glycosylphosphatidylinositol (GPI) anchored proteins are membrane bound proteins found throughout the animal kingdom. GPI anchored proteins are linked at their carboxyterminus through a phosphodiester linkage of phosphatidylethanolamine to a trimannosyl-non-acetylated glucosamine (Man3-GlcN) core. The reducing end of GlcN is linked to phosphatidylinositol (PI). PI is then anchored through another phosphodiester linkage to the cell membrane through its hydrophobic region. Intermediate forms are also present in high concentrations in microsomal preparations. The Man3-GlcN oligosaccharide core may undergo various modifications during secretion from the cell. GPI-anchored proteins include such as acetylcholinesterase, prion protein, CD24, CD55, CD58 and CD59. Most preferably, the GPI-anchored protein is CD24.

As used herein, "CD24" refers to a membrane glycoprotein with unusual lipid-like, organic-solvent soluble and heat-stable features (12). These characteristics are due to a small protein (mouse CD24 has 27 amino acids, human CD24 consists of 31 amino acids), extensive core N- or O-linked glycosylation, and the linkage to the cell membrane via a glycosyl-phosphatidylinositol (GPI)-anchor (12). In humans, CD24 is expressed by hematopoietic subpopulations of B and T lymphocytes but also on granulocytes and many carcinomas (for review see 13). Due to a GPI-anchor CD24 is exclusively localized in lipid-rafts (14).

Most preferably, the GPI-anchored protein is CD24 being further characterized by the REFSEQ Number NP_037362 (SEQ ID NO: 1)

The skilled artisan first might want to establish conditions allowing diagnostic purposes by exosome analysis, i.e. analyse whether CD24 positive exosomes are present in the fluid that should be characterized.

Thus, another embodiment of the present invention refers to a method to detect the presence of exosomes in an isolated fluid, wherein the exosomes are identified by biomarker detection. In a preferred embodiment, the exosomes are fetus-derived exosomes. In another preferred embodiment, the exosomes are tumor-derived exosomes. Moreover, in a preferred embodiment, the exosomes are ascites-derived exosomes.

In order to clearly distinguish fetus-derived exosomes from other membrane structures within the fluid to be analyse, the preferred biomarker is CD24. It can be detected by methods well-known to the person skilled in the art and further described supra.

Accordingly, the present invention further refers to isolated CD24-positive exosomes. It has been found by the inventors that the genetic information of the fetus is contained within those CD24 positive exosomes. Thus, these exosomes provide a valuable tool to enable the diagnosis, prognosis, and monitoring of various pathologic fetal or maternal conditions. CD24 positive exosomes can be isolated by methods known in the art. Briefly, exosomes are isolated and separated from the surrounding fluid by various centrifugation steps including (buoyant) density gradient centrifugation, followed by verifying the presence of the vesicles by CD24 detection. Particular preferred methods for exosome isolation are disclosed in the accompanying Examples, below.

In a further embodiment, the present invention refers to the use of CD24 as a biomarker to isolate exosomes from an isolated fluid.

The "fluid" includes whole blood, sweat, tears, ear flow, sputum, lymph, bone marrow suspension, lymph, urine, saliva, semen, vaginal flow, cerebrospinal fluid, brain fluid, ascites, milk, secretions of the respiratory, intestinal and genitourinary tracts, and amniotic fluid. Preferably, a fluid sample derived from an animal is urine or amniotic fluid. When analyzing a fluid from an animal, the animal can be, for example, a domesticated animal, such as a cow, a chicken, a pig, a horse, a rabbit, a dog, a cat, and a goat. In preferred embodiments, the animal is a human.

The present invention, furthermore, relates to a method for diagnosing malignant ascites comprising
  a) determining the presence or absence of tumor-derived exosomes in a sample of the ascites; and
  b) diagnosing malignant ascites based on the presence of tumor-derived exosomes in the sample of the ascites.

The term "diagnosing" as used herein refers to assessing the probability according to which an ascites is derived from a malignant tumor and, in particular, a malignant tumor having a poor prognosis. It is to be understood that the said assessment—although preferably—may not be correct for all subjects to be investigated by the method. However, it is envisaged that a statistically significant portion of population of subjects can be, preferably, correctly assessed. Whether a portion of subjects is statistically significant can be determined by statistical tests well-known in the art, in particular, Students t-test or Welsh-test. It is preferably envisaged that at least 70%, at least 80%, at least 90% or at least 95% of the subjects of a given cohort of subjects to be investigated by the method can be correctly assessed.

The term "malignant ascites" as used herein refers to ascites which is caused by or accompanies malignant tumors. Preferably, a malignant tumor is selected from the group consisting of ovarian carcinoma, breast carcinoma, non-small cell lung cancer, prostate carcinoma, colorectal cancer.

The presence of tumor-derived exosomes in the ascites sample can be determined by techniques set forth above. Preferably, tumor-derived exosomes can be detected in the ascites sample by using CD24 as a biomarker. It will be understood that the process of determination of the tumor-derived exosomes can also, preferably, comprise purification and/or isolation steps for the exosomes.

It has been found in accordance with the present invention that tumor-derived exosomes present in ascites samples are indicators for the malignancy of a tumor which gives raise to the ascites or accompanying the ascites. As set forth above, preferably, CD24 can be used as a biomarker for such tumor-derived exosomes. Consequently, tumor-derived CD24 positive exosomes can be used for diagnosing the malignancy of ascites and malignancy of the tumor underlying the ascites or accompanying it.

Preferably, at least one further biomarker selected from the group consisting of Annexin-1, EpCAM, ADAM10, CD9 and the cell adhesion molecule L1 will be determined in addition in the tumor-derived exosomes of the ascites sample. Among these markers, Annexin-1, ADAM10 and CD9 are bio markers for exosomes, in principle. The determination of such markers helps to identify and confirm the presence of exosomes, in principle, in the sample. The aforementioned EpCAM is a glycoprotein expressed on epithelial cells which is also overexpressed in carcinomas. Accordingly, the presence of EpCAM in tumor-derived exosomes in the ascites sample will be indicative for malignant ascites caused by or accompanying carcinomas. The cell adhesion molecule L1, likewise CD24, is a biomarker for malignant ascites in general. Therefore, the presence of the cell surface L1 protein in tumor-derived exosomes present in the ascites sample will be indicative for a malignant ascites caused by or accompanying tumors having a bad prognosis.

Thus, the present invention, in principle, pertains to the use of tumor-derived exosomes for diagnosing malignancy of ascites. Moreover, the present invention also contemplates the use of the aforementioned biomarkers present in tumor-derived exosomes for diagnosing whether a ascites is derived from a certain type of tumor, preferably a carcinoma. Further, the aforementioned biomarkers present in tumor-derived exosomes allow for predicting as to whether a diagnosis of a tumor causing the ascites or accompanying it is poor.

The diagnostic methods provided by the present invention will help to avoid cumbersome and cost intensive techniques for diagnosing or characterizing the aforementioned tumors based on e.g. biopsy samples. Moreover, it is an advantage of the diagnostic methods of the present invention to be carried out on ascites samples, i.e. samples which can be easily obtained from patients. Therefore, the severe side effects accompanying the use of biopsy samples, such as surgery complications, can be avoided.

The figures show:

FIG. 1 Identification of CD24 containing urinary vesicles (A) Two representative urine samples were either analyzed after TCA precipitation (left panel) or after ultracentrifugation at 100.000×g for 3 hrs. Pelleted vesicles (middle panel) or cleared supernatants (right panel) were analyzed by SDS-PAGE and Western blot analysis using mAb SWA11 to CD24 and ECL detection. (B) A representative pannel of CD24-containing urinary vesicles is shown. Membrane vesicles were obtained after ultracentrifugation of urine and analyzed by Western blot using mAb SWA11 to CD24 and ECL detection. F50: female 50 years old; M27: male 27 years old. (C) Membrane vesicles were analyzed for CD24, aquaporin-2 and HSP70 by Western blot analysis using respective antibodies.

Figure 2:
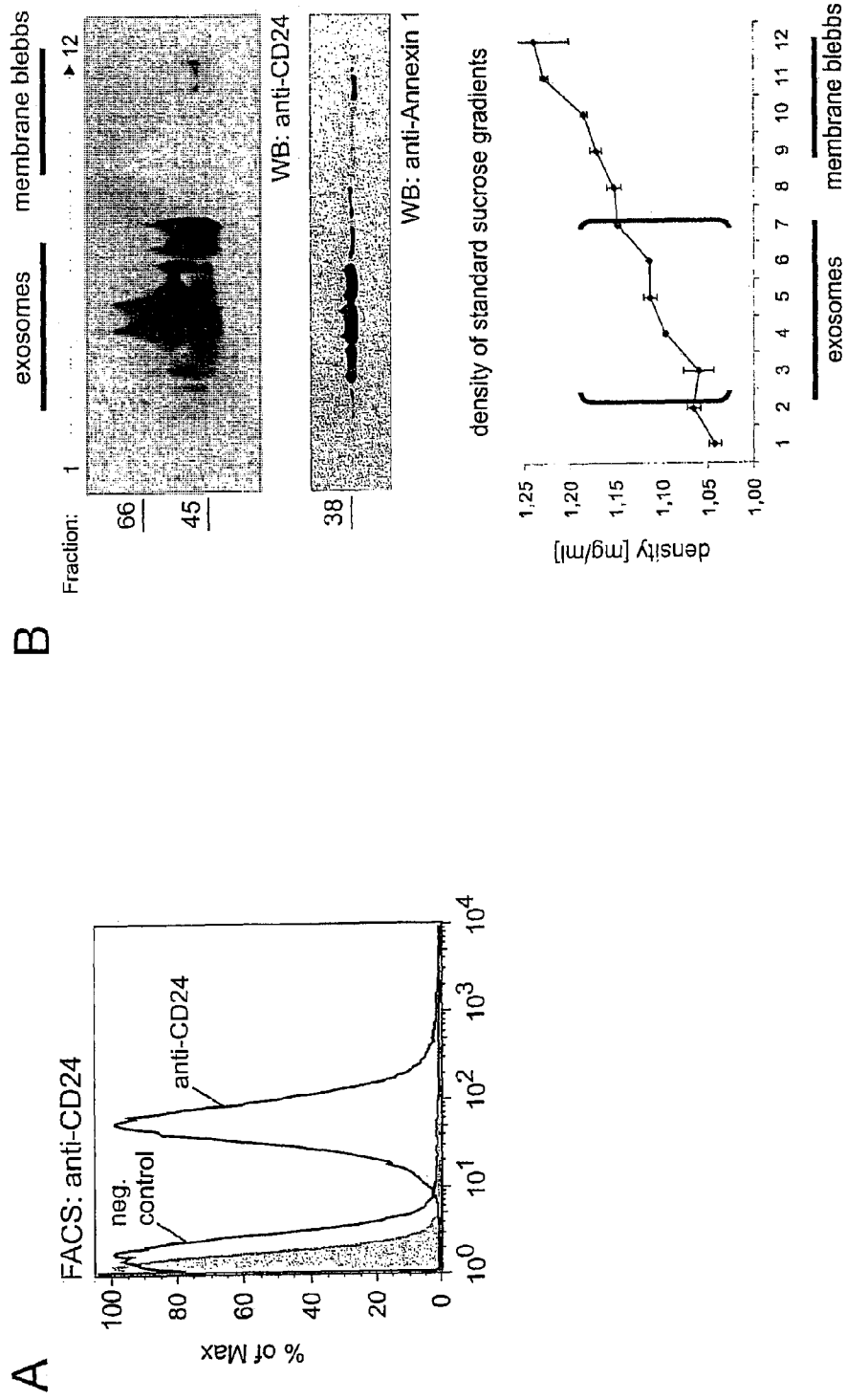
Figure 2:
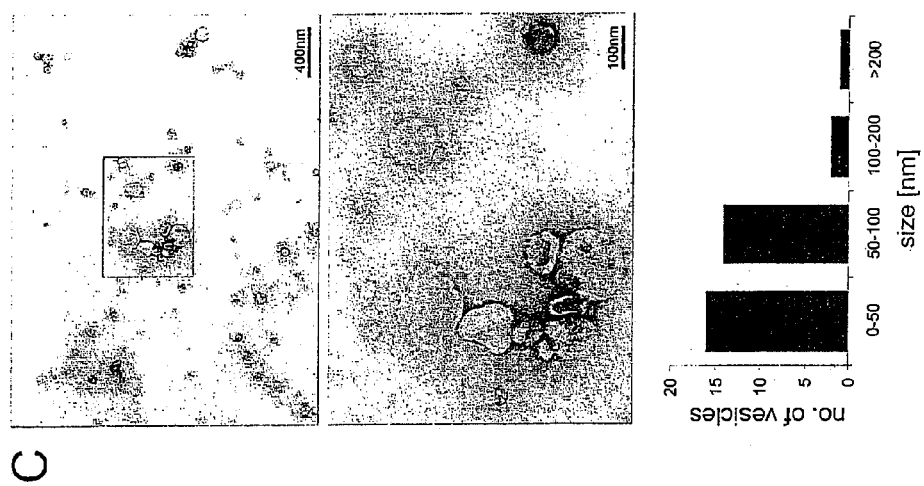

FIG. 2 Characterization of urinary vesicles (A) Exosomes isolated from urine were adsorbed to latex beads and stained for CD24 followed by PE-conjugated goat anti mouse IgG and FACS analysis. The negative control represent beads stained with the secondary antibody only. The grey curve represents the autofluorescence of unstained beads. (B) Exosomes were subjected to sucrose density centrifugation and the collected fractions from the gradient were analyzed by Western blot with the indicated antibodies to CD24 and the exosomal marker protein annexin-I followed by peroxidase-conjugated secondary antibody and ECL detection. The density of the gradient fractions is depicted in the graph below. (C) Electronmicroscopy pictures and size distribution analysis of urinary vesicles.

Figure 3:
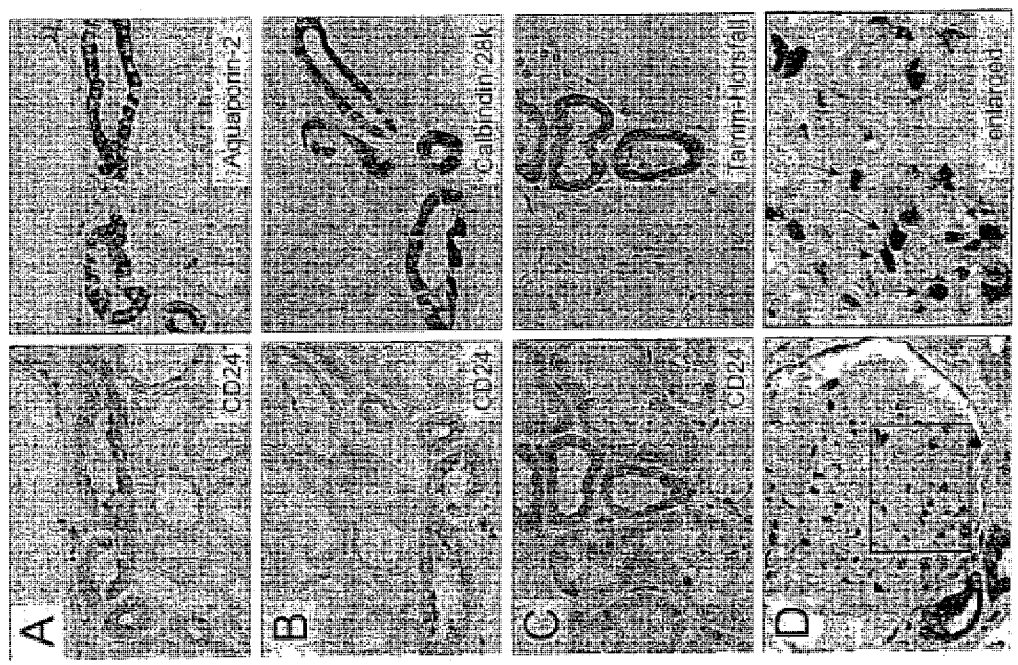
Figure 3:
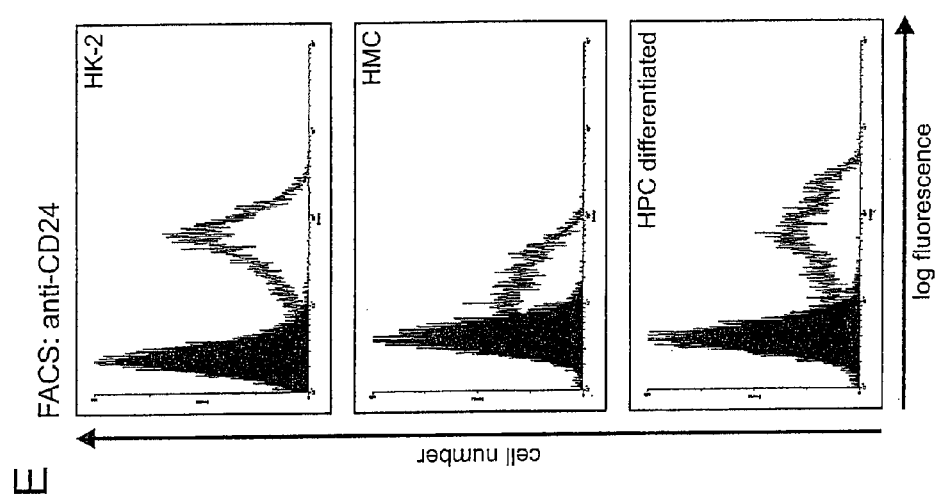

FIG. 3 Expression of CD24 in adult kidney

Expression of CD24 in adults kidney. Staining was carried out in combination with cell-type specific markers in serial sections. (A) Analysis of CD24 and aquaporin-2 (collecting duct); (B) CD24 and calbindin (distal tubules); (C) CD24 and Tamm-Horsfall (thick ascending limp of Henle loop). (D) Analysis of CD24 staining in glomeruli using the podocyte marker WT1 (blue) and SWA11 (red). Note the enlarged picture (right) marking double stained cells with arrows. (E) Cultured human tubular cells (HK-2), mesangial cells (HMC) or differentiated HPC were stained with mAb to CD24 followed by PE-conjugated goat anti mouse IgG and FACS analysis.

Figure 4:
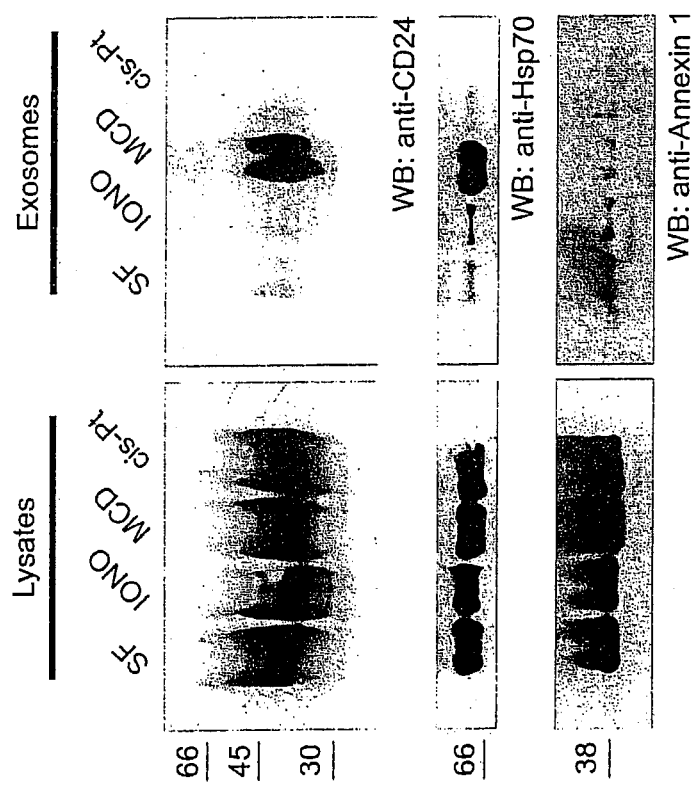

FIG. 4 Regulation of exosome secretion

Cultured HPC (differentiated) were treated with ionomycin (1 $\mu M$), MCD (10 mM) or cis-platin (15 $\mu M$) for 2 hr. Secreted membrane vesicles were harvested and cells were lysed in lysis buffer. Lysates and isolated vesicles were analyzed by SDS-PAGE followed by Western blot analysis with the indicated antibodies to CD24 and the exosomal marker proteins HSP70 and Annexin-1. Note the low level of constitutive vesicle secretion that is augmented by MCD.

Figure 5:
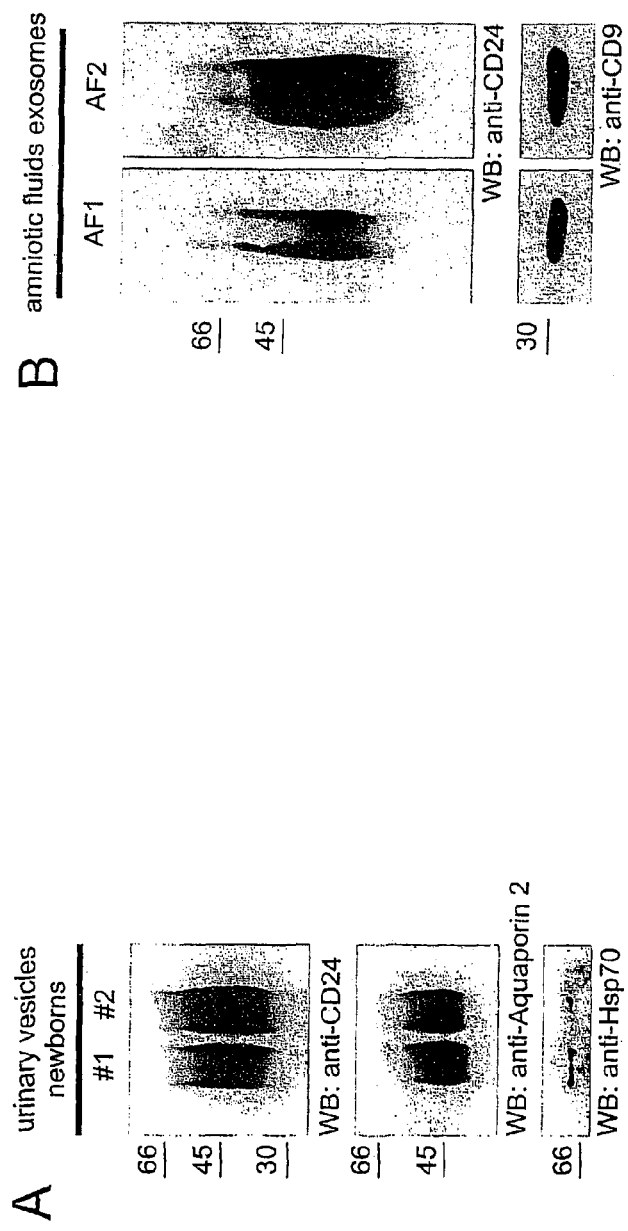

FIG. 5 CD24 containing exosomes in urine from newborn and amniotic fluid (A) Exosomes isolated from the urine of newborn were analyzed for CD24, aquaporin-2 and HSP70 by Western blot analysis. Two examples from n=5 samples with similar results are shown. (B) Exosomes isolated from the amniotic fluid of women undergoing amnioncentesis were analyzed for CD24 and CD9 by Western blot analysis. Two examples from n=4 with similar results are shown.

Figure 6:
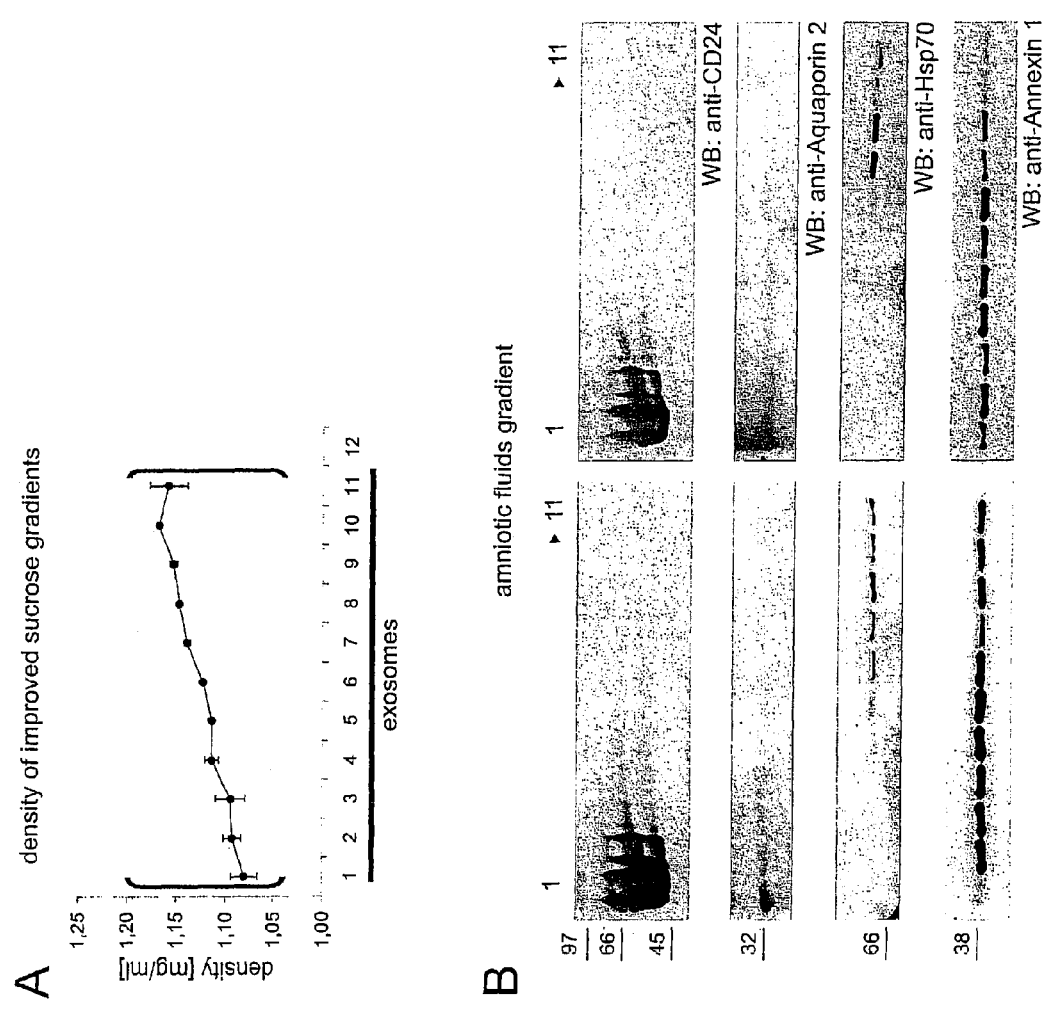

FIG. 6 Sucrose gradient analysis of exosomes from amniotic fluid (A) Density profile of an expanded sucrose gradient used for the analysis of human amniotic fluid. Note the expansion of exosomal fractions compared to the gradient shown in FIG. 2B. (B) Exosomes isolated from the amniotic fluid of women undergoing amniocentesis were analyzed for the indicated marker proteins by Western blot analysis.

Figure 7:
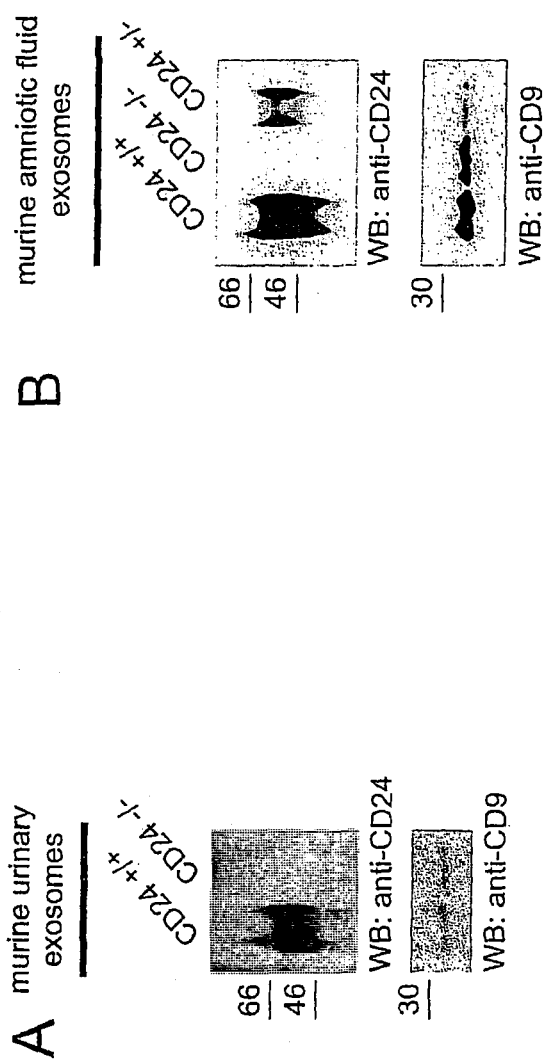

FIG. 7 CD24 containing exosomes in the urine and amniotic fluid of mice (A) Urine from C57B6 mice (CD24+/+) and CD24−/− mice were analyzed for CD24 and CD9 by Western blot analysis. Note that the CD9 signals are similar in both CD24+/+ and CD24−/− samples. (B) Amniotic fluid from pregnant CD24+/+, CD24−/− or CD24−/− female mice mated with CD24+/+males (CD24+/−) was analyzed for CD24 and CD9 by Western blot analysis.

FIG. 8 Ascites derived exosomes (A) Total vesicles of malignant ascites were purified by sucrose density centrifugation into a 40% sucrose/PBS cushion. Afterwards the isolated vesicles were separated due to their density in a discontinuous sucrose gradient. Resulting in the separation of the malignant ascites derived vesicles in exosomes and membrane blebs. The density of the sucrose gradient is shown. (B) Sixteen different ascites derived vesicles were separated by sucrose density gradients, following western blot analysis for different proteins: CD24, EpCAM and Annexin-1.

Figure 9:
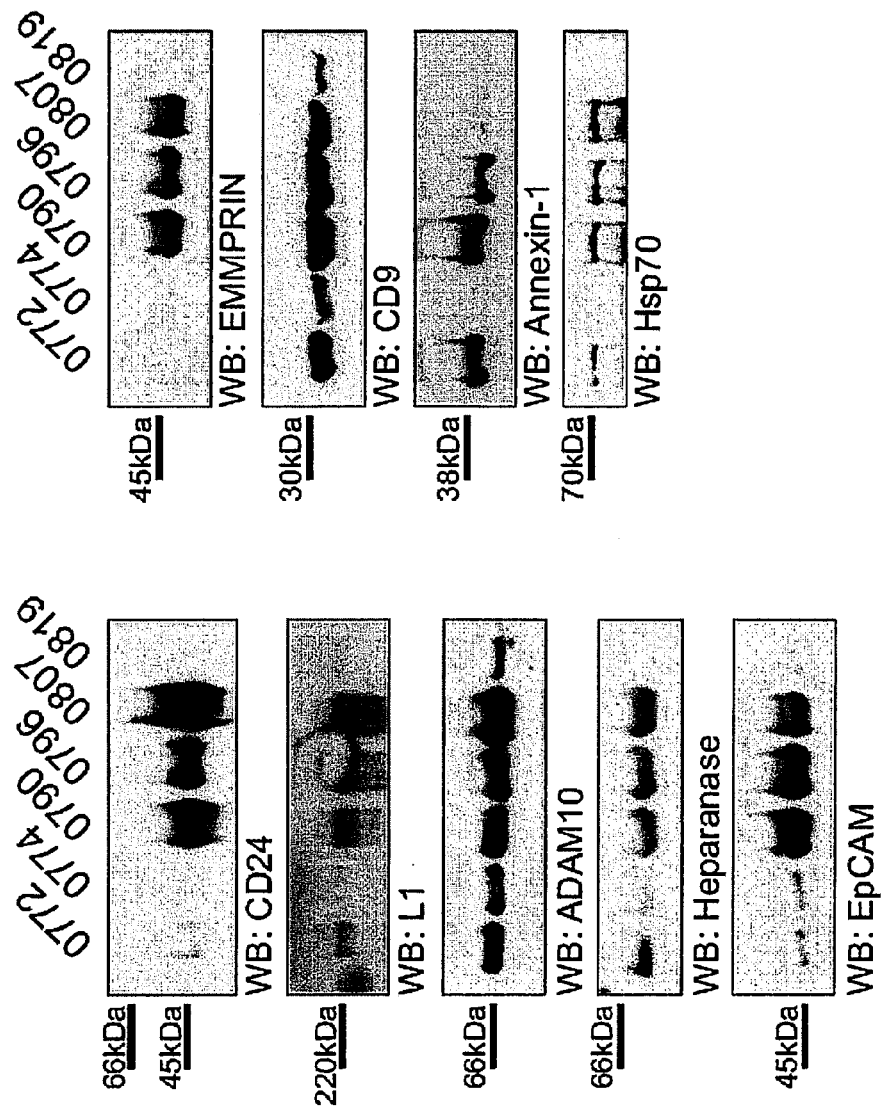

FIG. 9 Western blot analysis of exosomes

Exosomes were isolated by sucrose density gradient and the exosomal fractions 3-6 were pooled. Samples were analysed by SDS-PAGE and western blotting for the presence of different marker proteins.

Figure 10A:
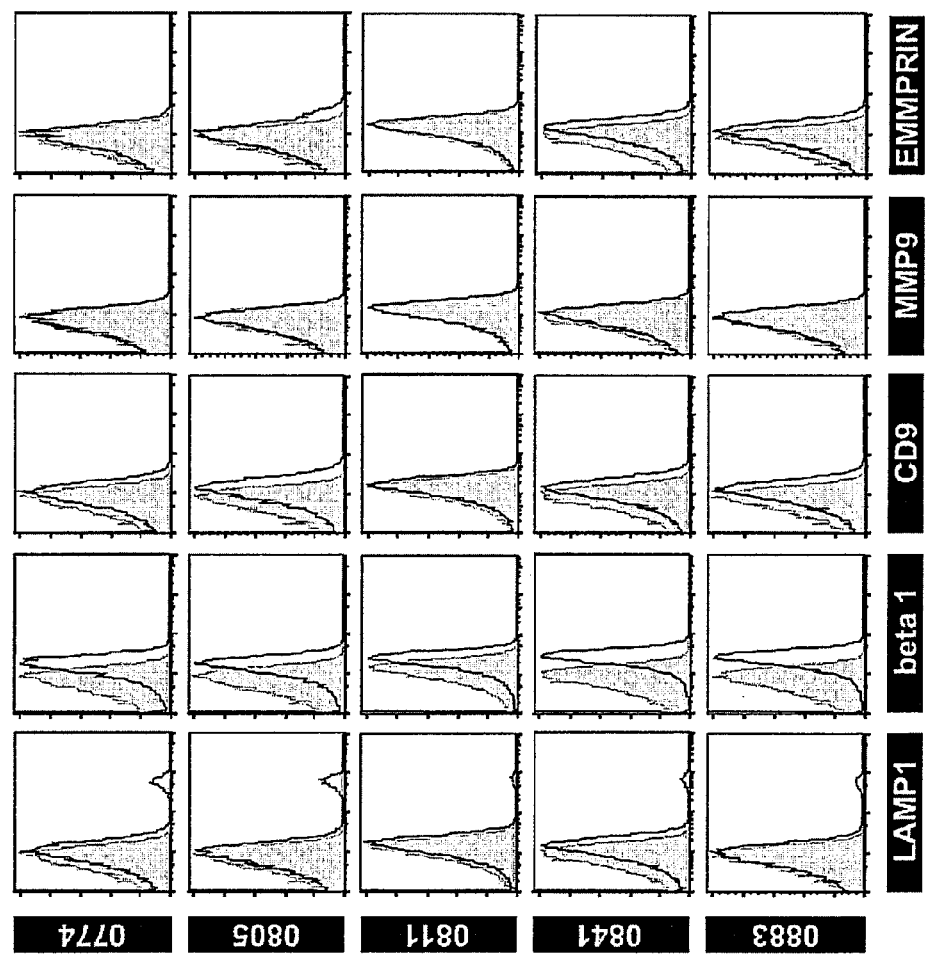
Figure 10B:
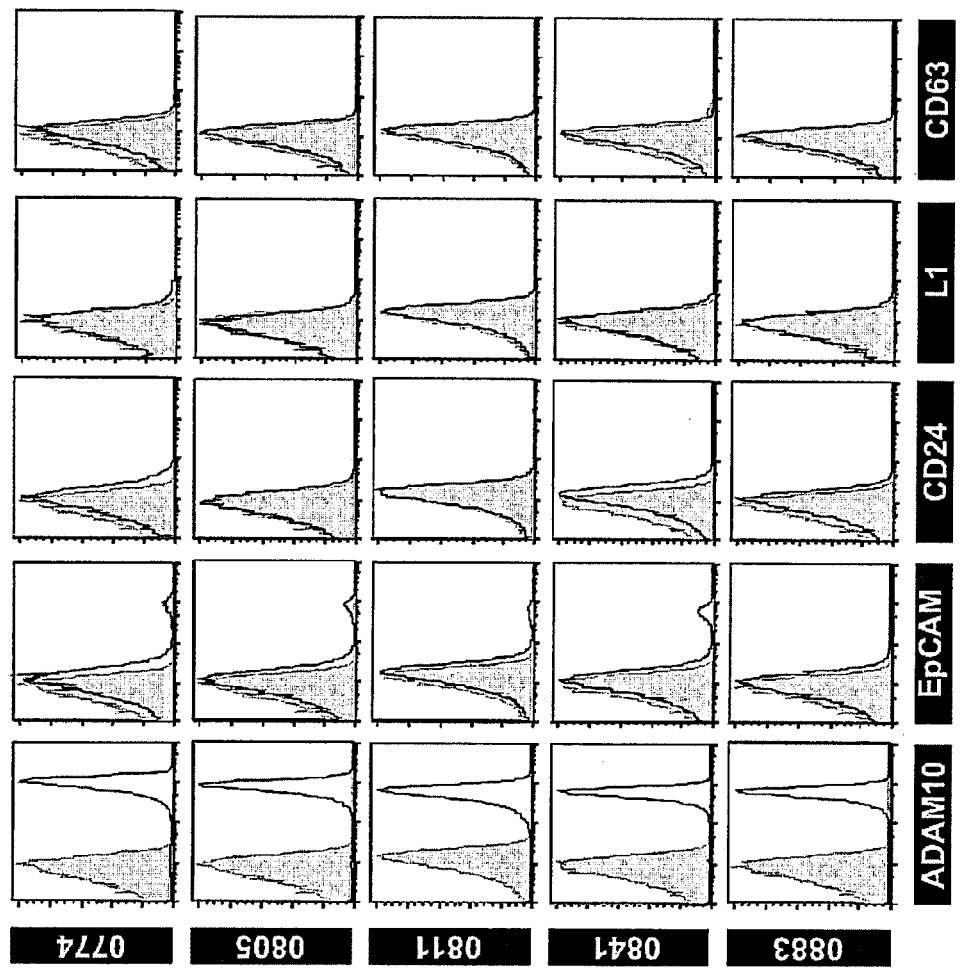

FIG. 10 Flow cytometry of exosomes (A) Flow cytometry profiles for five patient samples (0883, 0841, 0811, 0805 and 0774) are shown for the following markers: LAMP1, beta 1, CD9, MMP9and EMMPRIN. (B) Flow cytometry profiles for the same patient samples as in (A) are shown for the following markers: ADAM10, EpCAM, CD24, L1 and CD63.

Ascites derived exosomes were enriched by ultracentrifugation, bound to latex beads and analysed by flow cytometry for the surface expression of different proteins.

The invention is further illustrated by the following examples without being restricted to them:

EXAMPLE 1

CD24 Containing Exosomes in Urine of Adults

It was observed that the urine of healthy individuals contained significant amounts of CD24 as detected by Western blot analysis (FIG. 1A left panel). To find out whether CD24 was in a soluble or membrane bound form, urine was subjected to ultracentrifugation. The analysis of depleted supernatant and pelleted vesicles indicated that the CD24 activity was present in the 100.000×g pellet (FIG. 1A middle panel) but was not detected in the cleared supernatant (FIG. 1A right panel). The analysis was confirmed for n>30 individuals and representative examples are shown in FIG. 1B. Some individuals donated urine samples during the course of the day but only little variation in the amount of CD24-positive vesicles were noted. An average of 7.21 µg/ml (range 1.6-13 µg/ml, n=11) of protein was recovered per urine sample. Of appr. 120 samples analyzed only <5% were negative or low for CD24-vesicles content for reasons presently unknown (data not shown).

It was suspected that the pelleted material might represent membrane vesicles in the form of exosomes. Indeed, vesicles showed positive reactivity with antibodies to HSP70 (FIG. 1C), CD9 and annexin-I (see below). These antigens are enriched in exosomes (1,2). All samples were positive for the kidney marker aquaporin-2 that is known to occur in urinary exosomes (FIG. 1C).

Exosomes are released from cells by fusion of MVBs with the plasma membrane and have an orientation of cell surface antigens similar to the cell (1-3). To determine the orientation of antigens, urinary vesicles were immobilized onto latex beads and FACS analysis was carried out. Vesicles were readily stained with antibodies to CD24 (FIG. 2A). As detected by electronmicroscopy, the vesicles were of variable size ranging predominantly from 20 to 100 nm (FIG. 2C).

A sucrose density centrifugation was carried out in combination with Western blot analysis to further characterize the released membrane vesicles. Fractions in the middle part of the gradient (density 1.05-1.15 mg/ml) representing exosomes were positive for CD24 and annexin-I (FIG. 2B). It was concluded that the urinary vesicles containing CD24 had all characteristics of being exosomes.

EXAMPLE 2

Origin of CD24 Positive Exosomes

Marker analysis in adults has shown before that urinary vesicles are derived from distinct regions of the kidney (8). Using immunohistochemistry on serial sections, we investigated the expression of CD24 in human kidney in combination with defined cell subset markers. CD24 expression was observed in the aquaporin-2 positive collecting duct (FIG. 3A), in calbinin-positive distal tubular cells (FIG. 3B) and the Tamm-Horsfall positive thick ascending limp of the Henle loop (FIG. 3C). To examine whether podocytes were CD24-positive, two color staining using mAb WT1 against a podocyte specific nuclear antigen and SWA11 for CD24 was employed. As shown in FIG. 3D, double positive cells, but also CD24 single positive cells were clearly detected in the glomeruli.

The expression of CD24 in cultured cell lines derived from human kidney was also observed. Specifically, CD24 expression was observed by FACS analysis in immortalized human podocytes (HPC), the HK-2 human proximal tubular epithelial cell line and in mesangial cells (HMC) (FIG. 3C). These findings suggested that CD24 containing exosomes in the urine were likely derived from the kidney.

EXAMPLE 3

Regulated Exosomal Secretion in Human Podocytes

It was previously reported that the secretion of exosomes is constitutive but can be significantly enhanced in human tumor cells by exposure to substances such as the Ca-ionophore ionomycin, 4-aminophenylmercuric acetate (APMA), methyl-beta-cyclodextrin (MCD) or cis-platin (16,17). Differentiated HPC cells were treated with ionomycin (10 mg/ml), MCD (10 µg/ml) or cisplatin (1 µg/ml) and analyzed the amount of exosomes released. Only MCD significantly augmented the release of CD24 containing exosomes (FIG. 4). The vesicles contained the exosomal marker HSP70 but not annexin-I. These results suggest that the exosomal release can be regulated in HPC cells.

EXAMPLE 4

CD24 Exosomes are Present in Newborn Urine and Amniotic Fluid

It was observed that the presence of CD24-containing exosomes in urine samples was not restricted to adults but could also be found in infants. As shown in FIG. 5A, the urine of newborns contained significant amounts of CD24-positive exosomes that were both positive for aquaporin-2 and HSP70.

The renal system of the fetus contributes to the production of amniotic fluid. In order to analyze whether exosomes from the fetus were already released early in pregnancy, amniotic fluid collected at appr. week 16 of gestation for routine amniocentesis was examined. Indeed, in all (n=4) amniotic fluids tested exosomes containing CD24 and CD9 were detected (FIG. 5B). To analyze whether the CD24 positive exosomes were derived from the fetus, a refined sucrose gradient capable of separating distinct exosome subpopulations on the basis of bouyant density (see FIG. 6A) was used. The analysis revealed two populations of exosomes: a light fraction floating on top of the gradient (1.08-1.11 mg/ml) contained CD24, the kidney marker aquaporin-2, and annexin-I and a more dense fraction (1.11-1.14 mg/ml) containing only HSP70 and annexin-I (FIG. 6B). These results suggested that the CD24 positive exosomes were likely derived from the kidney of the fetus.

EXAMPLE 5

CD24 Exosomes in the Urine and Amniotic Fluid of Mice

It should be further examined whether or not CD24 was an essential component for vesicle formation. The human CD24 orthologue in the mouse is heat-stable antigen (HSA/mouse CD24) (12). CD24+/+ mice and CD24−/− mice were compared for vesicle release into the urine. Urinary vesicles were collected and analyzed by Western blot. As shown in FIG. 7A, in CD24+/− animals, exosomes were present in urine containing CD24 and CD9 whereas in CD24−/− animals the CD24 signal was missing. Given the identical band intensity of CD9 (FIG. 7A), and the identical protein content of exosomes (data not shown), it was concluded that CD24 was not essential for the process of exosomes secretion.

It was also investigated whether CD24 positive exosomes were present in mouse amniotic fluid. As shown in FIG. 7B and similar to the results in humans, CD24 positive exosomes were clearly detected in amniotic fluid of CD24+/+mice but were absent in CD24−/− mice. To unequivocally prove that the exosomes were derived from the fetus and not from the mother, CD24−/− female mice were crossed with wild-type male. This will give CD24+/− offspring in a CD24−/− mother. As shown in FIG. 7B, the amniotic fluid contained CD24 positive exosomes suggesting their origin from the fetus.

EXAMPLE 6

Discussion

Exosomes in human urine have been studied as a novel diagnostic means for kidney related diseases (8). By marker analysis it was shown that exosomes are derived from different kidney regions (8). Although exosomal analysis in human urine may offer novel diagnostic insights, a central question remains unaddressed: why are exosomes present in urine and what is the biological role of the exosomal secretion mechanism? Several possibilities could be envisaged: (i) exosome secretion from the kidney is important for the detoxification of the organism; (ii) the exosome secretion may be part of a protein and lipid degradation pathway in the kidney; (iii) exosome secretion is a primordial mechanism in adults but plays a role during fetal development when the kidney of the infant releases exosomes into the amniotic fluid.

Membrane vesicles in the form of exosomes are released from normal and cancer cells. In the present study vesicles present in human urine containing the GPI-anchored protein CD24 have been analyzed. It was found that i) CD24-vesicles are exosomes and are most likely derived from the kidney; ii) CD24-exosomes are present in newborne urine and in amniotic fluid of pregnant women and these vesicles are derived from the kidney of the infant; iii) CD24-exosomes are found also in the urine and amniotic fluid of mice; iv) in CD24−/− mice the secretion of vesicles into the urine is not affected suggesting that CD24 is not essential in the vesicle release process. The results suggest that exosomal secretion into urine and amniotic fluid is a biological process that is conserved over species barriers and could play a role in embryogenesis as well as in later life.

Clinical proteomics are extensively used to explore urinary biomarkers (18). A surprisingly high abundance of membrane-derived proteins was noticed in a recent study on total urinary proteins (19). This publication did not address the fact that urine contains both soluble proteins and urinary exosomes that contain plasma membrane proteins derived from the kidney and the urinary tract. Pisitkun et al. analyzed urinary exosomes using immunoelectron microscopy and proteomic analysis. They noticed that released exosomes were small (<100 nm) with variable size and were oriented "cytoplasmic-side inward" (8). The authors also identified by liquid chromatography-tandem mass spectrometry 295 proteins including proteins known to be involved in endosomal trafficking and exosome formation. In addition, there were cytoskeletal and motor proteins, many integral membrane proteins as well as 8 GPI-anchored proteins (8). The cytosolic proteins identified were presumably trapped in the lumina of forming exosomes. In the study, the density and orientation of urinary exosomes was similar to that reported by Pisitkun et al. (8). For unknown reasons the study by Pisitkun et al (8) did not identify CD24 as a component of urinary exosomes. This may be due to the unique feature of human CD24 being a highly glyocosylated mucin with a protein core of only 31 amino acids. These characteristics may have hampered the detection by proteomic analysis. Although the proteomic analysis of urinary exosomes can provide important information about the pathophysiology of the kidney, the biological relevance of the exosome secretion process remains unaddressed. Using CD24 as a marker, it was found that the presence of exosomes in the urine of adults is a constant feature with very little variation between individuals and during the course of the day. Importantly, it was found that exosomes are present in urine of newborns and can already be detected in the amniotic fluid of pregnant women undergoing amniocentesis, i.e. as early as 14-18 weeks after gestation. A separation technique based on bouyant density to further dissect the exosomes present in amniotic fluid was used. A fraction of exosomes that were lighter in density and contained the kidney marker aquaporin-2, CD24 and annexin-I was observed. These exosomes were most likely derived from the fetus. A second fraction of exosomes contained annexin-I and HSP70 but not CD24. It is possible that this subfraction originated from the mother. The fetal origin of CD24 exosomes was confirmed by genetic experiments in CD24 knockout mice.

One possibility is that exosome secretion from the kidney is important for the detoxification of the organism. Indeed, recent data in tumors have shown that exosomes or microvesicles with similar characteristics may cargo lipid solving drugs from tumors. An enhanced exosomal export of cisplatin and abnormal lysosomal trafficking of the cisplatin transporter was observed in drug-resistant human ovarian carcinoma cells (20). Experiments with doxorubicin and other small molecules confirmed drug accumulation and expulsion in shed vesicles (21). Moreover, there was an accumulation of drugs in membrane domains from which vesicles originated (21). It was proposed that by virtue of their hydrophobic character, these molecules can be shuttled to the plasma membrane via vesicle-mediated traffic, for final elimiation in complex with shed vesicles (21). If this was the case also in an organism, then exosomes could cargo lipophilic substances via the blood stream that are meant for secretion via the urine, such as steroids or other not water soluble substances. In fact, exosomes are present in blood plasma (8) and this has been confirmed in other studies.

Exosomes were also implicated in the regulation of immune responses (5,22). A role for exosomes in the modulation of T-cell signaling during pregnancy has been suggested (23). Exosomes obtained from the serum of pregnant women could suppress the expression of important T cell signaling components including CD3-ζ and JAK3. This suppression was correlated with exosome-associated FasL and a striking difference was noted between women delivering at term and those delivering pre-term (23). This study assumed a maternal origin of the isolated exosomes and did not take a possible fetal origin into account. The present study shows for the first time that fetal exosomes are present in amniotic fluid. As fetal cells are known to occur in the maternal blood circulation, it cannot be ruled out that also exosomes from the fetus are present in the bloodstream of the mother. Interestingly, exosomes display both immunostimulatory but also immunosuppressive properties (22). For example, exosomes produced by mouse dendritic cells pulsed with tumor peptide are able to mediate the rejection of established tumors (24). These antitumor effects were antigen-specific and were associated with the activity of T cells. Direct stimulation of T cells by membrane vesicles from antigen-presenting cells has also been reported (25). Conversely, it has been suggested that intestinal epithelial cells, T-cell tumors and melanoma cells can secrete exosomes capable of inducing antigen-specific tolerance and FasL-mediated T cell apoptosis (26). Exosomes derived from tumor cells were also shown to inhibit the cytolytic activity of NK cells by reducing the levels of perforin in NK cells, a molecule that is essential for target cell lysis (27). It is of interest to note, that a major fraction of cells in the amniotic fluid are decidual NK cells that play an important role in trophoblast invasion and the vascularisation of the uterus (28). In contrast to peripheral NK cells, decidual NK cells secrete a variety of cytokines but are non-cytolytic (28). It is tempting to speculate that exosomes may be involved in the inhibition of cytolytic activity of decidual NK cells similar to the tumor situation. Finally, a recent study has shown that exosomes can transport mRNA and microRNAs and represent a novel mechanism of genetic exchange between cell (29). For urinary exosomes future work will be required to closer analyze a possible role for nephron function. Also the immunological properties of fetal exosomes at the maternal-fetal interphase need to be investigated further.

In summary, the results describe the phenomenon of exosome secretion in the human renal system. The data provided on mouse CD24-exosomes in urine and amniotic fluid highlight that the secretion process is conserved over species borders. This similarity now allows experimental studies in animals to further unravel the biological role of exosome secretion.

EXAMPLE 7

Materials and Methods a) Chemicals and Antibodies

Antibodies to human CD24 (SWA11) and CD9 (TS9) were described (7,14). The mAbs to HSP70, annexin-I, and mouse CD9 were from BD-Transduction (Heidelberg, Germany). The antibodies to aquaporin-2 and calbindin 28K were from Sigma (Sigma, Taufkirchen Germany) and the antibody to WT1 (sc-846) was obtained from Santa Cruz (Heidelberg, Germany). The Tamm-Horsfall antibody was from Biotrend (Köln, Germany). The antibodies to mouse CD24 were described before (30).

b) Cell Culture and Animals

Human conditionally immortalized podocytes (HPC) were isolated and cultivated as previously described (31). Cells were grown in flasks either at the permissive temperature of 32° C. (in 5% $CO_2$) to promote cell propagation as a cobblestone phenotype (undifferentiated) or at the nonpermissive temperature of 37° C. (in 5% $CO_2$) to inactivate the SV40 T antigen and to allow the cells to differentiate. Prior to stimulation, cells were incubated for 16 h in RPMI 1640 medium, supplemented with 0.1 mg/ml of fatty acid-free bovine serum albumin. HK-2 human proximal tubular epithelial cells were obtained from American Type Culture Collection (ATCC, USA). Human mesangial cells (HMC) were kindly provided by Prof. Dr. Radeke (Depart. of Pharmacology, University of Frankfurt). Briefly cells were grown in RPMI-1640 medium supplemented with nonessential amino acids (1 ml/dl), L-glutamine (2 mM), sodium pyruvate (1 mM), transferrin (5 mg/ml), insulin (125 U/ml) and FCS (10%). Cells were grown at 37° C. in 5% $CO_2$. For passaging HMC were detached by trypsin-EDTA and split into 1:3. CD24−/− mice (C57BL6) were originally obtained from Dr. Peter Nielsen (Max-Planck Institute for Immunobiology, Freiburg, Germany) and maintained at the animal house of the DKFZ. Normal age-matched C57BL6 mice served as control.

c) Isolation of Vesicles from Urine

Urinary samples were obtained from healthy volunteers (male and female age range 22-57 years) and were collected during the course of a working day. Urine samples (50 ml from adults; 5 ml from newborn) were centrifuged for 10 min at 300×g and 20 min at 10000×g to remove cellular debris. Membrane vesicles were collected by centrifugation at 100.000×g for 2 or 18 h at 4° C. using a Beckman SW 40 rotor. Vesicles were directly dissolved in SDS sample buffer in relation to the original volume or processed further for gradient centrifugation (see below). Mouse urine was collected in metabolic cages. Drinking water contained 16% sucrose and urine (appr. 5 ml/16 h) was collected on ice. Mouse urine was processed as described above.

d) Isolation of Vesicles from Amniotic Fluid

Human amniotic fluids (n=4) were collected for routine amniocentesis and analyzed after removal of cells. Membrane vesicles were obtained after differential centrifugation as described above. Amniotic fluids from mice (apr. 100-500 µl) were collected on day 18 of gestation and were spun in an Eppendorf centrifuge at maximum speed for 20 min. The cell debris-free supernatant was diluted into 4 ml of PBS and vesicles were pelleted by overnight centrifugation using a Beckman SW60 rotor at 120.000×g. The vesicle pellet was taken up in SDS sample buffer.

e) Sucrose Density Gradient Fractionation

Vesicles isolated from ascites were loaded onto the top of a step gradient comprising layers of 2M, 1.3M, 1.16M, 0.8M, 0.5M and 0.25M sucrose as described (18). The gradients were centrifuged for 2.5 h at 100.000×g in a Beckman SW40 rotor. Twelve 1 ml fractions were collected from the top of the gradient and precipitated by chloroform/methanol or acetone as described (18). A modified sucrose gradient was designed to allow a more refined analysis of exosomes according to differences in density.

f) FACS Analysis

FACS analysis of isolated vesicles was done after adsorbing of isolated vesicles to 4 µm (Surfactant-free) aldehyde-sulfate latex beads (Interfacial Dynamics Corp., Portland Oreg., USA) as described (32). The staining of beads or cultivated cells with mAbs and PE-conjugated secondary antibodies has been described (14,18). Stained beads or cells were analyzed with a FACScan using Cellquest software (Becton & Dickinson, Heidelberg, Germany).

g) Immunohistochemistry

This was described previously (33). Briefly, paraffin tissue sections were deparaffinized and antigens were retrieved for 20 min by incubating the tissue sections in 0.01 M sodium citrate buffer, pH 6.0, in a microwave (500 Watt). The intrinsic peroxidase activity was abolished by pretreatment in 3% $H_2O_2$ in methanol for 30 min at RT. After blocking the sections were incubated with a Avidin/Biotin Blocking Kit (Linaris, Wertheim, Germany) following the manufactor's protocol. The sections were incubated overnight with CD24 antibody (SWA11 hybridoma supernatant diluted 1:5 in blocking reagent). After washing the slides, the Universal Quick Kit (Linaris) was used for staining. As substrate the AEC Substrate Kit from BioGenex (California, USA) was used to detect immune complexes. To counterstain the sections, slides were incubated with hematoxylin (Roth, Karlsruhe, Germany). For doublestaining CD24 with WT1, a specific podocyte marker, sections were not counterstained with hematoxylin. WT1 antibody was diluted 1:250 in blocking reagent (1% BSA in PBS) and incubated overnight. After washing the sections, the alkaline phosphatase-conjugated goat-anti rabbit antibody (1:250 diluted in blocking reagent) was added for 1 hour at 37° C. Endogenous alkaline phosphatase was blocked with levamisole (Sigma, Taufkirchen, Germany) before adding the substrate. The immune complex was detected adding the Sigma Fast™ BCIP/NBT (Sigma) substrate tablet until a blue color developed.

h) Biochemical Analysis

SDS-PAGE under reducing conditions and transfer of proteins to an Immobilon membrane using semi-dry blotting has been described (14,18). After blocking with 5% skim milk in TBS, the blots were developed with the respective primary antibody followed by peroxidase conjugated secondary antibody and ECL detection.

EXAMPLE 8

Analysis of Ascites Derived Exosomes

Malignant ascites contains a large amount of vesicles and soluble proteins derived from both tumor and healthy tissue. One type of vesicles that can be isolated from malignant ascites are exosomes. Exosomes are small membranes (50-100 nm) of endosomal origin and can be secreted by tumor cells. It has been shown, that exosomes different proteins in a biological active form.

Figure 8A:
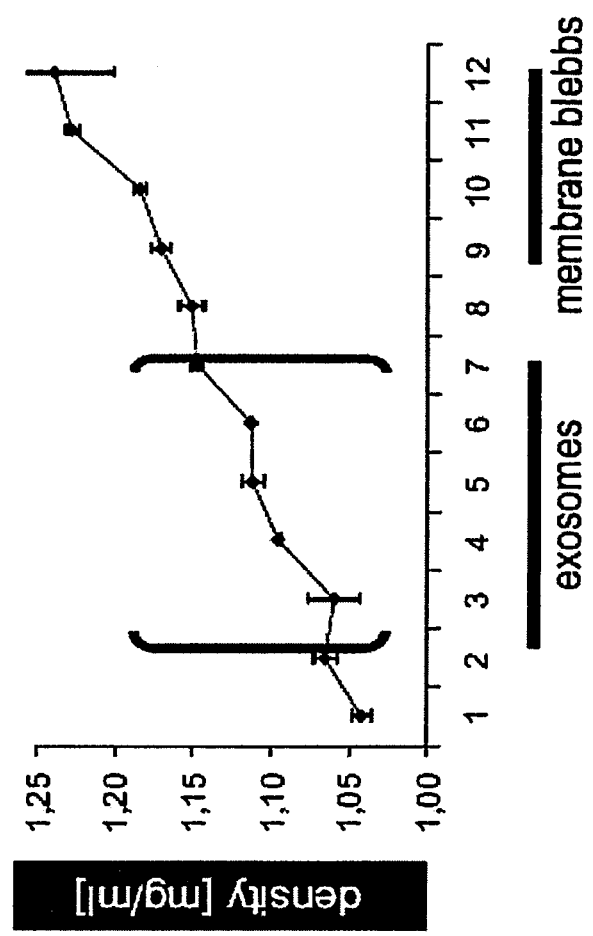
Figure 8B:
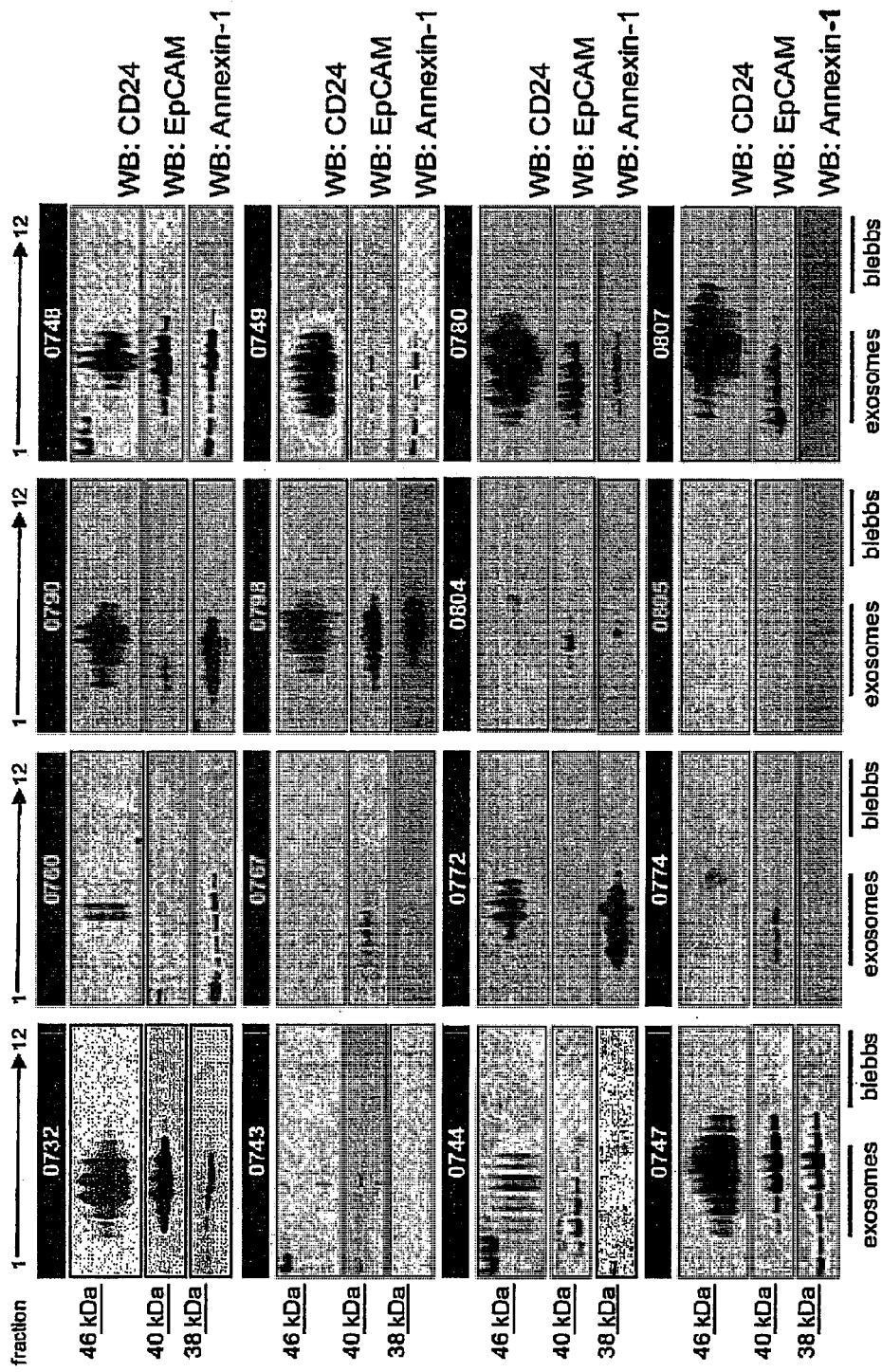

For separation of vesicles from soluble proteins ultracentrifugation onto a 40% sucrose cushion was used. Isolated vesicles include exosomes with a diameter of 50 to 100 nm and microvesicles or apoptotic membrane blebbs with a diameter of 100 to 1000 nm. These subtypes of vesicles can be separated due to their density in a discontinuous sucrose density gradient. After ultracentrifugation each gradient was collected from the top to the bottom into 12 fractions (FIG. 8A). Exosomes are located in the fractions 3-6 with a density of app. 1.06 to 1.12 mg/ml, whereas microvesicles float at fraction 9-12 with density of app. 1.16 to 1.25 mg/ml. The vesicles in the sucrose fractions were harvested, precipitation by acetone and separated on a 10% SDS-PAGE followed by western blotting. FIG. 8B shows sixteen different ascites derived vesicle gradients, that were checked for the protein expression of CD24, EpCAM and Annexin-1. The glycoprotein CD24 is a marker for poor prognosis in different tumors e.g. ovarian carcinoma, breast carcinoma, nonsmall cell lung cancer, prostate carcinoma, colorectal cancer and others. CD24 can be detected in the ascites derived exosomes and co-localizes with Annexin-1, a protein widely used as a marker for exosomes. Moreover these exosomes contain EpCAM a glycoprotein expressed in epithelial tissues that is overexpressed in carcinomas. The gradients show no protein in the microvesicle fractions indicating that the major type of vesicles in ascites from ovarian carcinoma patients are exosomes.

To analyse the protein content of ascites derived exosomes, fractions 3-6 were pooled after sucrose gradient separation and analysed the samples again for the presence of different marker proteins by SDS-PAGE and western blotting (FIG. 9). The analysed exosomes show different protein expression patterns for examined molecules, indicating that this pattern could allows a type of tumor staging. Both the metalloprotease ADAM10 and the tetraspanin CD9 seemed to be a good exosomes marker protein for all samples. Some samples are enriched in CD24 and the cell adhesion molecule L1 (e.g. 0790, 0796, 0807), which is also associated with a bad prognosis in different cancers. Others are positive for the exosomal markers Annexin1 and Hsp70 but show no CD24 and L1 signal (0772).

Another technique for the analysis of exosomes is flow cytometry. This method allows to identify proteins located on the surface or in the membrane of exosomes. Therefore exosomes were enriched by ultracentrifugation and bound to Latex-beads. After blocking and staining with first and secondary antibody the Latex-beads bound exosomes were analysed by a FACS Canto II instrument.

REFERENCES

1. Thery C, Zitvogel L, Amigorena S, Exosomes: composition, biogenesis and function. *Nat Rev Immunol* 2002; 2:569-579.

2. Andre F, Schartz N E, Movassagh M, et al. Malignant effusions and immunogenic tumour-derived exosomes. *Lancet* 2002; 360:295-305.
3. Raiborg C, Rusten T E, Stenmark H: Protein sorting into multivesicular endosomes. *Curr Opin Cell Biol* 2003; 15:446-455.
4. Ginestra A, La Placa M D, Saladino F, et al. The amount and proteolytic content of vesicles shed by human cancer cell lines correlates with their in vitro invasiveness. *Anticancer Res* 1998; 18:3433-3437.
5. Keller S, Sanderson M P, Stoeck A, et al. Exosomes: from biogenesis and secretion to biological function. *Immunol Lett* 2006; 107:102-108.
6. Caby M P, Lankar D, Vincendeau-Scherrer C, et al. Exosomal-like vesicles are present in human blood plasma. *Int Immunol* 2005; 17:879-887.
7. Gutwein P, Stoeck A, Riedle S, et al. Cleavage of L1 in exosomes and apoptotic membrane vesicles released from ovarian carcinoma cells. *Clin Cancer Res* 2005; 11:2492-2501.
8. Pisitkun T, Shen R F, Knepper M A, Identification and proteomic profiling of exosomes in human urine. *Proc Natl Acad Sci USA* 2004; 101:13368-13373.
9. Stoorvogel W, Kleijmeer M J, Geuze H J, et al. The biogenesis and functions of exosomes. *Traffic* 2002; 3:321-330.
10. de Gassart A, Geminard C, Hoekstra D, et al. Exosome secretion: the art of reutilizing nonrecycled proteins? *Traffic* 2004; 5:896-90.
11. Dolo V, Ginestra A, Cassara D, et al. Selective localization of matrix metalloproteinase 9, beta1 integrins, and human lymphocyte antigen class I molecules on membrane vesicles shed by 8701-BC breast carcinoma cells. *Cancer Res* 1998; 58:4468-4474.
12. http://mpr.nci.nih.gov/PROW/guide/270610370_g.htm
13. Kristiansen G, Sammar M, Altevogt P, Tumour biological aspects of CD24, a mucin-like adhesion molecule. *J Mol Histol* 2004; 35:255-262.
14. Schabath H, Runz S, Joumaa S, et al. CD24 affects CXCR4 function in pre-B lymphocytes and breast carcinoma cells. *J Cell Sci* 2006; 119: 314-325.
15. de Gassart A, Geminard C, Fevrier B, et al. Lipid raft-associated protein sorting in exosomes. *Blood* 2003; 102: 4336-4344.
16. Gutwein P, Mechtersheimer S, Riedle S, et al. ADAM10-mediated cleavage of L1 adhesion molecule at the cell surface and in released membrane vesicles. *Faseb J* 2003; 17: 292-294.
17. Stoeck A, Keller S, Riedle S, et al. A role for exosomes in the constitutive and stimulus-induced ectodomain cleavage of L1 and CD44. *Biochem J* 2006; 393: 609-618.
18. Hoorn E J, Pisitkun T, Zietse R, et al. Prospects for urinary proteomics: exosomes as a source of urinary biomarkers. *Nephrology* 2005; 10: 283-290.
19. Adachi J, Kumar C, Zhang Y, et al. The human urinary proteome contains more than 1500 proteins, including a large proportion of membrane proteins. *Genome Biol* 2006; 7:R80.
20. Safaei R, Larson B J, Cheng T C, et al. Abnormal lysosomal trafficking and enhanced exosomal export of cisplatin in drug-resistant human ovarian carcinoma cells. *Mol Cancer Ther* 2005; 4:1595-1604.
21. Shedden K, Xie X T, Chandaroy P, et al. Expulsion of small molecules in vesicles shed by cancer cells: association with gene expression and chemosensitivity profiles. *Cancer Res* 2003; 63: 4331-4337.
22. Li X B, Zhang Z R, Schluesener H J, et al. Role of exosomes in immune regulation. *J Cell Mol Med* 2006; 10: 364-375.
23. Taylor D D, Akyol S, Gercel-Taylor C, Pregnancy-associated exosomes and their modulation of T cell signaling. *J Immunol* 2006; 176:1534-1542.
24. Zitvogel L, Angevin E, Tursz T, Dendritic cell-based immunotherapy of cancer. *Ann Oncol* 2000; 11: 199-205.
25. Kovar M, Boyman O, Shen X, et al. Direct stimulation of T cells by membrane vesicles from antigen-presenting cells. *Proc Natl Acad Sci USA* 2006; 103:11671-11676.
26. Andreola G, Rivoltini L, Castelli C, et al. Induction of lymphocyte apoptosis by tumor cell secretion of FasL-bearing microvesicles. *J Exp Med* 2002; 195:1303-1316.
27. Liu C, Yu S, Zinn K, et al. Murine mammary carcinoma exosomes promote tumor growth by suppression of NK cell function. *J Immunol* 2006; 176: 1375-1385.
28. Hanna J, Goldman-Wohl D, Hamani Y, et al.: Decidual NK cells regulate key developmental processes at the human fetal-maternal interface. *Nat Med* 2006; 12:1065-1074.
29. Valadi H, Ekström K, Bossios A, et al. Exosome-mediated transfer of mRNAs and microRNAs is a novel mechanism of genetic exchange between cells. *Nature Cell Biol* 2007; in press DOI: 10.1038/ncb1596
30. Kadmon G, Eckert M, Sammar M, et al. Nectadrin, the heat-stable antigen, is a cell adhesion molecule. *J Cell Biol* 1992; 118: 1245-1258.
31. Saleem M A, O'Hare M J, Reiser J, et al. A conditionally immortalized human podocyte cell line demonstrating nephrin and podocin expression. *J Am Soc Nephrol* 2002; 13: 630-638.
32. Blanchard N, Lankar D, Faure F, et al. TCR activation of human T cells induces the production of exosomes bearing the TCR/CD3/zeta complex. *J Immunol* 2002; 168: 3235-3241.
33. Fogel M, Gutwein P, Mechtersheimer S, et al. L1 expression as a predictor of progression and survival in patients with uterine and ovarian carcinomas. *Lancet* 2003; 362: 869-875.

The invention claimed is:

1. A method for detecting the presence of exosomes in an isolated fluid comprising identifying the exosomes in the isolated fluid by detecting the presence of CD24-marker on the exosomes.

2. The method of claim 1, wherein the exosomes are fetus-derived exosomes.

3. The method of claim 1, wherein the exosomes are tumor-derived exosomes.

4. The method of claim 3, wherein at least one further biomarker is detected, said at least one further biomarker being selected from the group consisting of: Annexin-1, EpCAM, ADAM10, CD9 and the cell adhesion molecule L1.

5. The method of claim 3, wherein the presence of tumor-derived exosomes is indicative for malignant ascites.

6. A method for prenatal diagnosis to detect congenital anomalies of a fetus comprising the steps of:
 (a) isolating exosomes from an isolated fluid sample, and
 (b) detecting pathological fetal conditions from the exosomes isolated in the fluid sample;
 wherein (i) the exosomes are identified by biomarker detection, (ii) the biomarker is CD24, (iii) the isolated fluid sample containing the exosomes is derived from or originated from the fetus, and (iv) the CD24-positive exosomes carry fetal genetic information which provides prenatal diagnosis of congenital anomalies in the fetus.

7. The method of claim 6, wherein the isolated fluid sample is one of the group consisting of amniotic fluid, urine and serum.

8. The method of claim 6, wherein said exosomes are fetus-derived exosomes.

9. An isolated exosome, wherein the exosome comprises a CD24-marker.

10. The exosome of claim 9, wherein the exosome is obtainable by a method comprising the steps of isolating exosomes from an isolated fluid sample and identifying the exosomes by CD24-marker detection.

* * * * *

UNITED STATES PATENT AND TRADEMARK OFFICE
CERTIFICATE OF CORRECTION

PATENT NO.        : 8,568,994 B2
APPLICATION NO.   : 12/671196
DATED             : October 29, 2013
INVENTOR(S)       : Altevogt et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 747 days.

Signed and Sealed this
Twenty-first Day of April, 2015

Michelle K. Lee
*Director of the United States Patent and Trademark Office*